United States Patent [19]

Miller, Jr.

[11] Patent Number: 4,527,421
[45] Date of Patent: Jul. 9, 1985

[54] DYNAMIC SURFACE TENSIOMETRY AND METHOD

[75] Inventor: Theodore E. Miller, Jr., Midland, Mich.

[73] Assignee: The Dow Chemical Company, Midland, Mich.

[21] Appl. No.: 570,331

[22] Filed: Jan. 13, 1984

[51] Int. Cl.$^3$ .......................................... G01N 13/02
[52] U.S. Cl. ...................................................... 73/64.4
[58] Field of Search ........................................ 73/64.4

[56] References Cited

U.S. PATENT DOCUMENTS

| | | | |
|---|---|---|---|
| 3,426,584 | 2/1969 | Smith | 73/64.4 |
| 3,881,344 | 5/1975 | Jobe | 73/64.4 |
| 4,416,148 | 11/1983 | Klus et al. | 73/64.4 |

FOREIGN PATENT DOCUMENTS 817533 3/1981 U.S.S.R. ............................ 73/64.4

OTHER PUBLICATIONS

A. M. Kragh, Trans. Faraday Soc. 60 (Part I), pp. 225–232, (1964), Effect of Gelatin and Salts on the Dynamic Surface Tension of Manoxol OT.
W. C. Meyer, Preprint AIME Annual Meeting, Atlanta, GA, Mar. 6–10, 1983, Application of Dynamic Surface Tensiometry to Froth Flotation.
A. K. Gaigalas et al, AIChE Journal 28, pp. 922–928, (1982), Time Dependence of Pressure in a Bubbler Tube.

*Primary Examiner*—Tim Miles
*Attorney, Agent, or Firm*—William M. Yates; Burke M. Halldorson

[57] ABSTRACT

An improved apparatus and method are disclosed for measuring the dynamic surface tension at a gas-liquid interface by the maximum bubble pressure method. The gas is bubbled out an orifice tube dipped in the liquid; the maximum pressure in each bubble is a function of the surface tension. In the invention, the rate of gas flow is raised continually to increase the rate of bubbling at least several fold over a few minutes. The varying pressure of the bubbling gas is measured continuously by an instantaneous transducer. Electronic circuits respond to the transducer and provide signals indicative of the maximum bubble pressure and of the rates of bubbling. A recorder responds to the signals and displays a spectrum of the maximum bubble pressure in units indicative of surface tension as a function of the bubbling rate. Measurements may be taken over more than a thousand bubbles in each spectrum. The rise in gas pressure is achieved by passing gas from a source under pressure in series through two flow-restricting capillaries, with an accumulator zone between.

11 Claims, 6 Drawing Figures

DYNAMIC SURFACE TENSIOMETRY AND METHOD

FIELD OF THE INVENTION

This invention relates to improved apparatus and method for measuring dynamic surface tension at a gas-liquid interface by the maximum bubble pressure method.

BACKGROUND OF THE INVENTION

The measurement of surface tension is important for understanding and controlling physico-chemical behavior at gas-liquid and other interfaces. In industry, typical applications include the formulation of detergents, preparation of emulsions, and concentration of ores by froth flotation.

Surface tension is commonly measured using static, equilibrium techniques such as the duNouy tensiometer. Yet in many applications involving rapid or brief contact of dispersed phases, surface equilibrium is not reached. For such, static measurements may be of little value, since they do not reveal transient or rate-limited phenomena in which surface tension may be changing rapidly, e.g., in emulsification and in ore flotation.

To study these, dynamic surface tension measurement is required. A dynamic procedure frequently used is the maximum bubble pressure method. In it, gas is passed through an orifice tube into the test liquid, forming a succession of bubbles. The inflation pressure inside each bubble is at a maximum when the bubble achieves minimum radius of curvature. This occurs as the bubble assumes hemispherical shape at the orifice. The maximum bubble pressure is thus directly related to, and provides a true measure of, the surface tension of the liquid. (W. J. Moore, Physical Chemistry, 3rd Ed., p. 729-31, Prentice Hall, N.J., 1962.)

This method has been used to study transient surface behavior of aqueous surfactant solutions. For some solutions, the observed value of dynamic surface tension is not constant but changes when the rate of bubbling is altered. The change, which differs from one surfactant to another, has been attributed to diffusion phenomena and used to study them. Tensiometers for making appropriate measurements have been described. (A. M. Kragh, Trans. Faraday Soc. 60 (1), p. 225-232 (1964); U.S. Pat. No. 3,881,344 (1975). Cf. U.S. Pat. No. 3,426,584 (1969).)

Using these instruments, maximum bubble pressure is observed as a value averaged over a number of bubbles generated at a fixed rate. When more than one rate is to be studied, the rate of bubbling must be changed manually, and another maximum pressure average value taken. The averaging makes for insensitivity to small or rapid changes in maximum bubble pressure, and the instruments to not admit of easy, precise control and change of bubbling rate. In addition, the technique is slow and cumbersome for determining changes in maximum bubble pressure over a wide range of bubbling rates.

SUMMARY OF THE INVENTION

The present invention provides improvements in the apparatus and procedure for measuring dynamic surface tension by the maximum bubble pressure method. Results may be obtained automatically, rapidly, and reliably, even by operators of limited training. Maximum bubble pressure readings are not averaged, but are taken continuously during runs of a thousand or more bubbles made over a very few minutes. The rate of bubbling is not held constant throughout each run but is increased continually and automatically from a low value up to nearly the maximum physically possible, ten or more hertz. Maximum bubble-pressure measurements are recorded as a spectrum of values in units directly indicative of dynamic surface tension and displayed as a function of the frequency of bubble formation.

The new instrument, in common with known bubble tensiometers, has an orifice tube adapted to be immersed in the test liquid at a predetermined depth. Gas is passed through it to form a stream of bubbles, the maximum pressure in each bubble being a function, and indicative, of the dynamic surface tension. In the invention, automatic means deliver gas to the orifice tube at a rate rising continually over a short interval of time to increase the frequency of bubble formation at least several fold. Pressure-sensitive means measure the maximum pressure bubble throughout the interval.

The continually rising gas flow is provided by an automatic system including a supply of gas under pressure. In flow-series with the supply are a first flow-restricting capillary, an accumulator zone for storing gas from the first capillary, a second flow-restricting capillary, and a relatively unrestrictive delivery tube connecting the second capillary to the bubble tube.

The pressure measuring system includes a high speed pressure-sensitive transducer in free communication with the bubble tube. The transducer provides electrical output instantaneously indicative of the varying internal pressure in each bubble throughout its formation and release. A peak-detecting circuit responsive to the transducer output provides a signal indicative of the maximum attained bubble pressure. A converter circuit responsive to the transducer output provides a signal indicative of the frequency of bubble formation. A recorder, connected to respond to these two signals, is adapted to display a spectrum of the values of the maximum bubble pressure in units directly indicative of surface tension as a function of the frequency of bubble formation. The spectrum constitutes the ultimate reading of the new instrument.

By studying a series of such spectra made with a test liquid during a group of controlled experiments, much may be learned about the surface behavior of the liquid.

BRIEF DESCRIPTION OF THE DRAWINGS

The invention may be explained with reference to the accompanying drawings in which.

DETAILED DESCRIPTION OF THE INVENTION

(A) Apparatus

Figure 1:
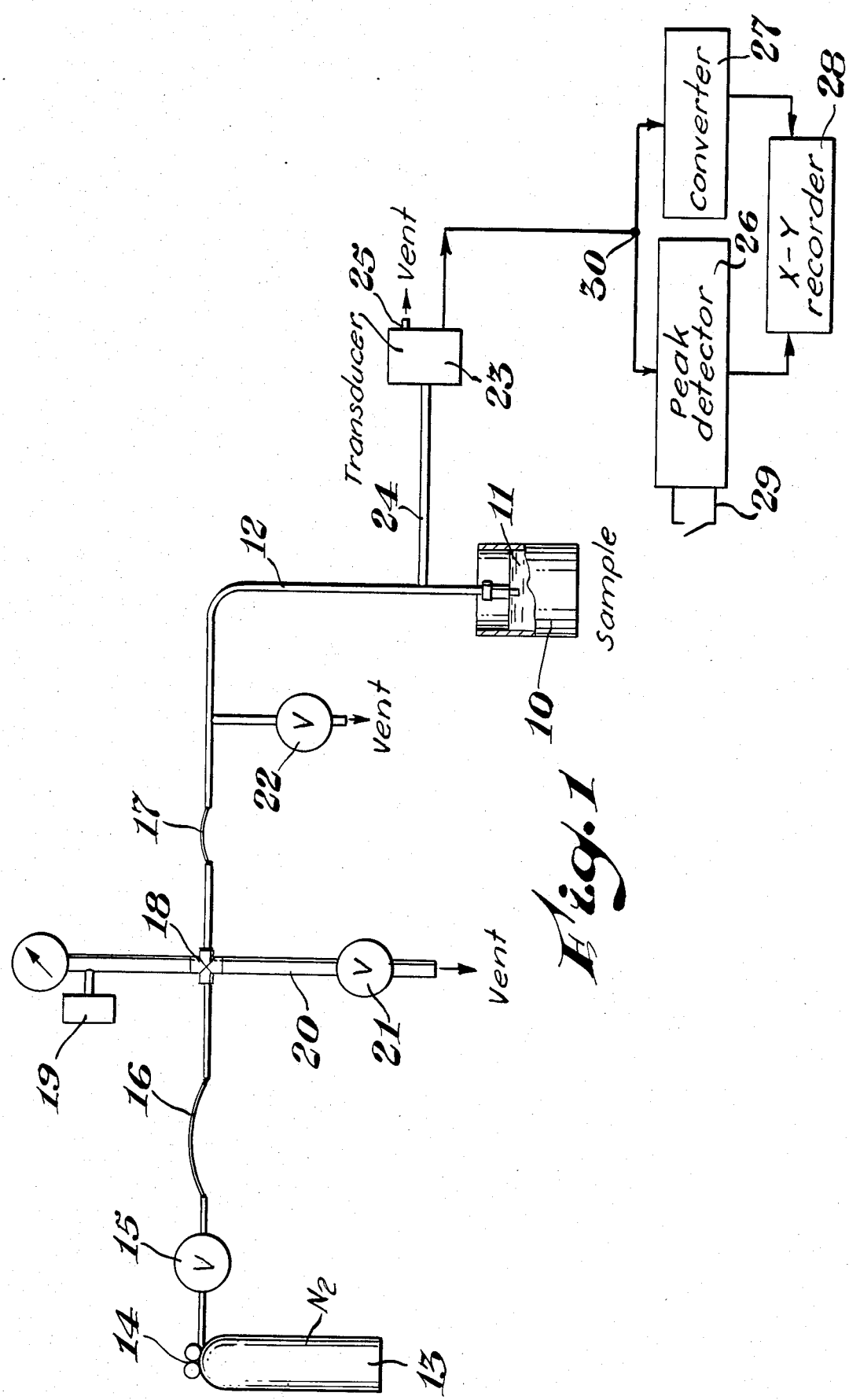
FIG. 1 is an overall schematic diagram of the invention in a preferred embodiment.

A tensiometer according to the invention is shown schematically in FIG. 1. The liquid undergoing test to determine its dynamic surface tension is placed in a beaker 10 large enough not to interfere with free bubbling, e.g., 30 ml. A bubble orifice tube 11 is immersed in the liquid to a predetermined depth, such as 10 mm. A flow of gas passes through the bubble tube from a supply system by way of a small but relatively unrestricted delivery tube 12.

The gas, conveniently dry nitrogen, comes from a pressure cylinder 13 fitted with a reducing control valve 14 and (optionally) a shutoff valve 15. In flow series between the gas source and the delivery tube 12 are a first flow-restricting capillary 16, an accumulator zone, and a second flow-restricting capillary 17. As shown, the accumulator zone consists of a four-way tee 18 in gas communication with the two capillaries, a Bourdon gauge, a reservoir 19, and a tube 20 ending in a normally-open solenoid-operated vent valve 21. A second similar valve 22 allows venting the gas supply tube 12.

As gas flows through the orifice tube 11 forming a succession of bubbles, the pressure inside each bubble at every instant before detachment is monitored by a pressure-measuring and recording system. The key element of the system is a high speed differential-pressure transducer 23. One side of the transducer is in unrestricted communication with the orifice 11 by way of a short tube 24 connected into the gas supply tube 12. The other side of the transducer is open to the atmosphere through a vent 25. The electrical (voltage) output of the transducer is connected as input to a peak detector circuit 26 and a converter circuit 27. The output signals from these two circuits are led to an X-Y recorder 28 which traces a spectrum (cf. FIG. 5), as will be described later.

A switch 29 may be closed momentarily across the electronic circuitry to reset it to starting condition when it is desired to begin a new measuring cycle. Actuating another switch operates solenoids to close the vents 21 and 22 at the start of each cycle and hold them closed until a second actuation releases them at the end of the cycle.

The transducer 23 is advantageously of the capacitive type. It should be high speed, i.e., have a rapid response time, in order to follow the variations in pressure in each bubble. It should also be highly sensitive, nearing fully electrical output at a differential pressure approximating the higher bubbling pressure expected. Suitable in the invention is a commercial diaphragm-capacitive model, Baratron type 223A (MKS Instruments Inc., Burlington, Mass.), with an inherent frequency of 40 kilohertz, outputting 10 volts at a pressure differential of ten Torr (ten mm. of mercury).

Figure 2:
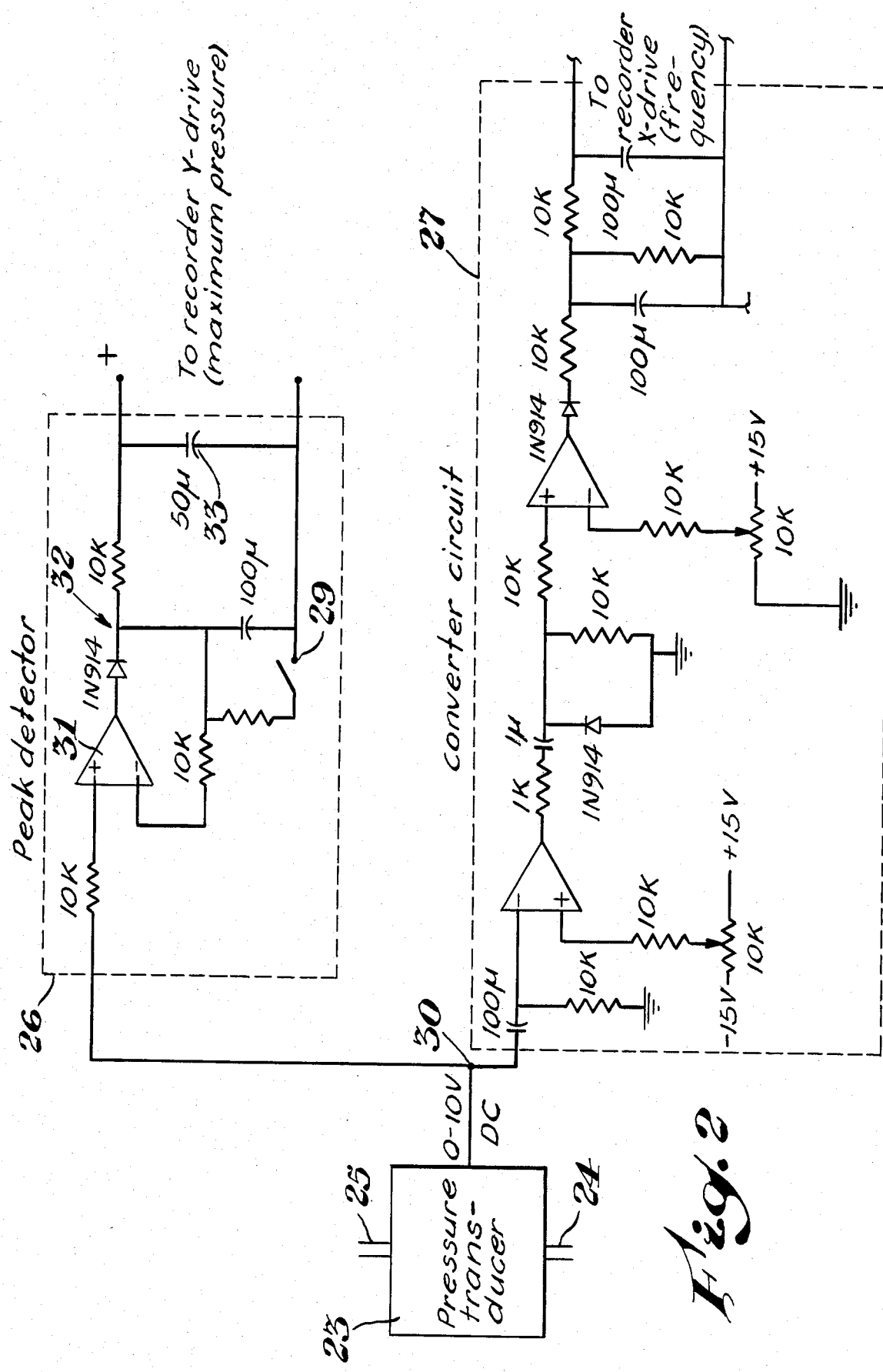
FIG. 2 is a diagram of the electronic peak-detector and converter circuits indicated by boxes in FIG. 1.
Figure 3:
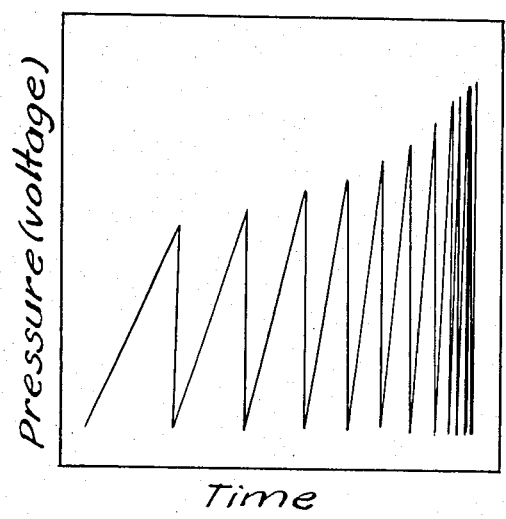
FIG. 3 is a schematic oscilloscope trace of the raw voltage output of the pressure transducer in FIG. 1 during a bubbling sequence.

The varying output signal of the transducer 23 may, when desired, be observed by connecting an oscilloscope (not shown) at a measuring point 30 (FIG. 2). A schematic trace of one such signal is in FIG. 3. The voltage indicative of internal pressure in each bubble rises to a peak (the maximum pressure) and drops back. The peaks come steadily closer together as the bubbling rate increases. For a surfactant solution, as in FIGS. 5 and 6, the peaks also ramp upwardly as the rate increases.

The peak detector 26 and converter 27 circuits, of known design, are shown schematically in FIG. 2. In the peak detector, the varying transducer signal is inputted to an amplifier 31. The amplifier output is converted by a diode circuit 32 to a series of unidirectional voltage pulses. The circuitry monitors the peak value of each pulse and stores that voltage in a capacitor 33. Thus, the voltage in the capacitor remains essentially constant whenever the maximum bubble pressure stays constant during a bubbling run or ramps upwardly when maximum bubble pressure increases, until the run is completed. The capacitor voltage is indicated continuously on the Y-drive of the recorder 28.

The converter circuit 27 also monitors the transducer output signal, noting the frequency of the peaks occasioned by bubbling. It performs a frequency-to-voltage conversion and transfers that voltage to the input of the X-drive of the recorder 28, where it is indicated in terms of frequency. Frequency-to-voltage converter circuits are available commercially on semi-conductor chips.

The X-Y recorder 28 is a standard instrument in which both the X- and Y- drives are voltage-responsive. Together the drives control the positioning of a pen which draws a spectrum on a chart.

In the apparatus of FIG. 1, the orifice tube 11 preferably has non-wetted (hydrophobic for aqueous solutions) surfaces and is squared off at its tip to minimize capillary effects that might distort formation of fine spherical bubbles. Conveniently, it is a short length of Teflon (polytetrafluoroethylene) or polyethylene tubing. The bore should be small enough to allow smooth rapid bubbling but not so fine as to impose substantial restriction to gas flow, e.g., 0.02 to 0.04 inch (0.5 to 1.0 mm), with 0.03 to 0.045 inch (0.76 to 1.14 mm) preferred. A preferred bubble tube is one-half inch (13 mm) long with internal diameter 0.031 inch (0.79 mm), with a tip formed at the lower end by expanding the tubing internally approximately 2 mm to an inside diameter of 0.040 inch (1.0 mm).

The gas delivery system may also be made of Teflon tubing. The delivery tube 12 and connector tube 24 should be large enough to allow relatively unrestricted gas flow. They may, for instance, be 0.031 inch (0.8 mm) i.d. and 0.063 inch (1.6 mm), respectively. The tubing 20 forming the gas accumulator zone should be somewhat larger, e.g., ⅛ inch (3 mm) i.d. The flow-restricting capillaries 16 and 17 are much finer, to allow precise control of the gas flow rate. The first capillary 16 should preferably have a flow resistance higher than that of the second 17. The capillary may be steel tubing of 0.005 inch (0.13 mm) i.d., the length of the first being five inches (126 mm) and of the second one inch (25 mm).

(B) Operation

In making surface tension measurements with the apparatus illustrated, the beaker 10 is positioned with the bubble orifice tube 11 immersed in the test liquid to a depth predetermined during calibration, as will be explained. While there is some tolerance, it is desirable over a series of runs to set the depth for all runs the same within a precision of about one mm.

The nitrogen flow system is started by opening the inlet valves 14 and 15. Gas enters through the capillary 16 but flows out the open vents 21 and 22; the accumulator zone at 18 and the supply tube 12 stay at atmospheric pressure. The reset switch 29 is then actuated, zeroing the electronic circuits, and the vents 21 and 22 are closed electrically. Nitrogen entering through the capillary 16 is no longer free to escape. Pressure begins to rise slowly in the accumulator zone, the value being shown by the Bourdon gauge 19. A part of the accumulated gas begins to flow through the capillary 17 into the delivery tube 12 and thence to the bubbler tip 11. Soon after the gas pressure at the tip exceeds the hydrostatic pressure corresponding to the depth of immersion, bubbles begin to form and escape. The varying internal pressure in each bubble is monitored by the transducer 23. Maximum bubble pressure and frequency of bubbling are detected continuously by the electronic circuits 26 and 27, the values being displayed on the chart of the recorder 28.

As a run proceeds, the continuing inflow of gas through the first capillary 16 causes the pressure in the accumulator zone to rise steadily. (With the nitrogen valve 14 regulating at 50 psig (340 kPa), the accumulator may reach 10 psig (70 kPa)). As a result, the rate of gas flow through the second capillary 17 into and through the delivery tube 12 also rises steadily. Despite this increasing flow rate, since the gas delivery tube 12 is comparatively unrestricted relative to the capillary, the pressure in it does not rise much; it remains at a low value dictated by the depth of immersion of the bubble tip 11 and the maximum pressure in the bubbles as they form. However, because of the steadily increasing gas flow, the rate of bubble formation continues to rise as long as the vents 21 and 22 stay closed. (This rise in mass flow rate, though continuous, is not necessarily linear with time.) The maximum rate of gas flow is self-limiting due to the capillary size which in the system described limits bubbling rates to about 12 bubbles per second or less. The bubbling run may be terminated by the reopening of vents 21 and 22. At this, the gas confined in the accumulator zone escapes, and the supply system is ready for the next bubbling run.

With a bubbler tip and gas supply system of the preferred size stated, rise of gas flow through the tip (and the corresponding increase in bubbling rate) occurs over about one to about three minutes. During this interval at least a thousand bubbles form. The frequency of bubbling increases several fold, e.g., from substantially less than one to the maximum physically possible before jetting supplants bubbling. This maximum is at least ten hertz and may be more with some test liquids.

It will thus be appreciated that, in contrast to prior practice, the apparatus of the invention measures a spectrum of maximum bubble pressures as a function of a steadily increasing frequency of bubbling throughout a test run of short duration but comprehending at least a thousand separate bubbles.

(C) Calibration

1. Y-Drive

The maximum internal pressure in a gas bubble forming at an orifice in a test liquid is the sum of two components, one hydrostatic and the other due to surface tension. The relation for an immersed circular orifice is $$P = \rho g h + 2\gamma/R \tag{1}$$

where

P = maximum internal pressure (dynes/cm$^2$)

$\rho$ = density difference between liquid and gas (gm/cm$^3$)

g = acceleration of gravity (980 cm/sec$^2$)

h = height of liquid above orifice (cm); depth of immersion $\gamma$ = surface tension of liquid (dynes/cm)

R = radius of orifice, which equals bubble radius at maximum pressure.

The equation may be rewritten $$\gamma = R(P - \rho g h)/2 \tag{2}$$

For a given instrument according to the invention, the radius R is a constant, and may be measured with a microscope. Gravity g is constant. The depth of immersion h may be held constant from run to run by careful placement of the orifice at the same predetermined depth. The density $\rho$ stays nearly the same for a series of dilute aqueous solutions and may be determined when needed. With all these parameters constant or known, by equation (2) the surface tension $\gamma$ of a test liquid becomes a direct function of the maximum internal pressure P.

In the invention, the pressure P is indicated by the transducer output and is recorded as voltage in the Y-drive of the recorder 28. For an instrument with the transducer and circuitry detailed specifically above, and with a bubble orifice of inner radius 0.049 cm immersed in every test to the same depth of 1.0 cm, equation (2) becomes $$\gamma = 33.4V - 24.01\rho \tag{3}$$

where

V is volts.

Calibration may be made or verified for any similar instrument by test runs on water and other pure liquids of known surface tension. With the calibration, the Y-drive of the recorder 28 may be marked directly in units of surface tension (dynes/cm).

2. X-Drive

Figure 4:
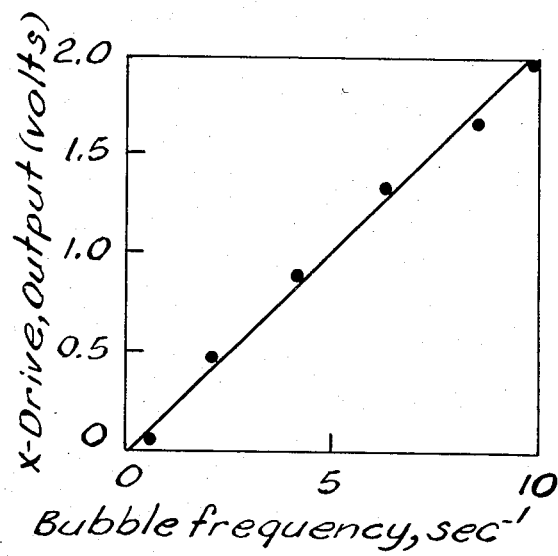
FIG. 4 is a frequency-to-voltage calibration curve of the output of the converter circuit of FIG. 2.

As explained, in the invention the converter circuit 27 provides a voltage output indicative of the frequency of bubbling. This output is recorded on the X-drive of the recorder 28. Calibration may be made by observing voltage with a separate meter while independently determining the bubbling rate. The rate may be checked by timing bubbles with an electronic counter/timer with microsecond resolution (Tektronix TM 500) connected temporarily at the measuring point 30. A typical frequency-to-voltage calibration curve is shown in FIG. 4. With this calibration, the intervals along the X-drive may be marked directly in terms of frequency of bubbling.

(D) Results

In a series of experimental runs, the preferred instrument of the invention was used to observe the dynamic surface tension of a number of test liquids over a range of bubble frequencies. Operation was as described, with surface tension (dynes/cm) being charted on the recorder as a function of bubbling frequency.

In all runs, nitrogen was the gas. Runs were made at room temperature (21° C.). Duration of each was two to three minutes, at bubble frequencies rising steadily from below one to above ten hertz. More than a thousand bubbles were monitored in each run. Charts made during the runs are shown in FIGS. 5 and 6.

As seen from the charts, measurements made with water alone show that the measured value of dynamic surface tension does not change with increase in bubble frequency. Tests with other pure (i.e., one-component) liquids show the same invariance. (The chart for water shows slight droop at bubble frequencies above 10 hertz. This is apparently due to a slight Bernoulli effect and can be increased or reduced by varying the orifice diameter of the probe 11).

Figure 5:
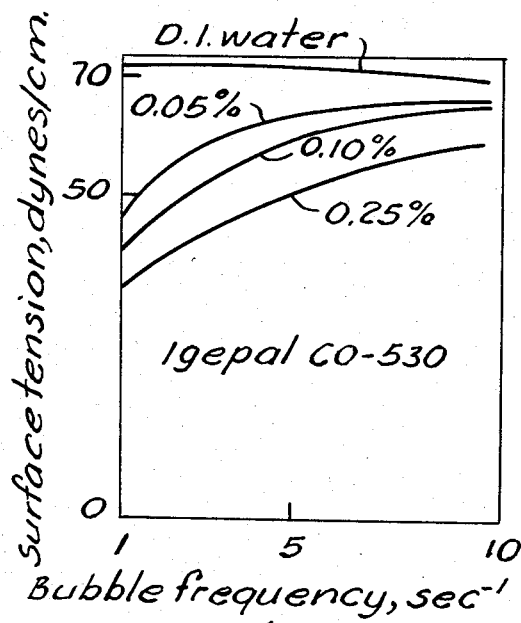
FIG. 5 is a chart made by the recorder in FIG. 1, on which the observed dynamic surface tension values of several test liquids are plotted as a function of bubble frequency.

FIG. 5 also reports a series of runs on deionized water containing various small concentrations of a nonionic surfactant sold as Igepal CO-530 (nonyl phenol ethoxylated with six mols of ethylene oxide). Under static conditions, and at bubble frequencies up to one hertz, the surfactant causes a marked decrease in surface tension. However, as bubble frequencies rise, the dynamic surface tension rises steadily. The detergent action of the surfactant is thus shown as distinctly less effective when surface contact times are very brief.

Figure 6:
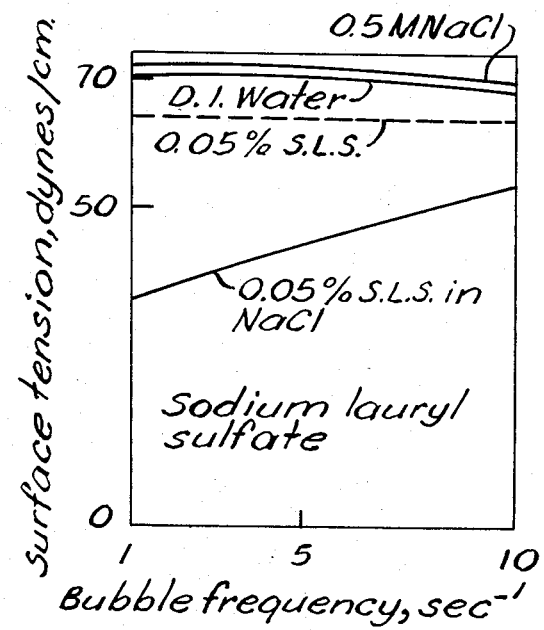
FIG. 6 is a similar chart for a different group of test liquids.

FIG. 6 shows a series of runs on deionized water alone, water containing 0.05 percent by weight of the anionic surfactant sodium lauryl sulfate (SLS), water containing sodium chloride (0.5M NaCl), and water containing both SLS and NaCl. NaCl increases the dynamic surface tension of water slightly, and SLS depresses it, but both effects are essentially independent of bubbling rate. However, when both NaCl and SLS are in solution, the dynamic surface tension is dramatically lowered at low bubbling rates but rises steadily as bubbling rate increases above one hertz.

Runs on cationic surfactants show results similar to those of FIG. 5. The frequency-dependence for all classes of surfactants is attributed to limitations on the rate at which larger molecules can diffuse to and reach the gas-water interface as it is forming. Runs over a range of liquid temperatures show that dynamic surface tension at the same bubble rate is reduced as temperature increases, and that the frequency-dependence is flattened.

From the foregoing, it will be apparent that the instrument of the invention is useful in studying dynamic surface tension phenomena of a wide variety of liquid systems of industrial and scientific concern. One such study, using the instrument of the invention but not describing it, has recently been reported by applicant's colleague Wilfred C. Meyer ("Application of Dynamic Surface Tensiometry to Froth Flotation", AIME Annual Meeting, Atlanta, GA, Mar. 6–10, 1983).

What is claimed is:

1. Apparatus for measuring dynamic surface tension at a gas-liquid interface by the maximum bubble-pressure method comprising
   a bubble orifice tube adapted to be immersed in the liquid at a predetermined depth;
   automatic means for delivering the gas to the orifice tube at a rate rising continually over an interval of time to increase the frequency of bubble formation at least several fold; and
   automatic means for measuring the maximum bubble pressure throughout the interval, each such pressure being a function of the surface tension.

2. Apparatus according to claim 1 in which the pressure-measuring means includes a transducer in free communication with the bubble tube and providing electrical output instantaneously indicative of the pressure in each bubble.

3. Apparatus according to claim 2 including
   a peak-detecting circuit responsive to the transducer output providing a signal indicative of the maximum bubble pressure;
   a converter circuit responsive to the transducer output providing a signal indicative of the frequency of bubble-formation; and
   a recorder responsive to the said two signals and adapted to display a spectrum of values of the maximum bubble pressure in units directly indicative of surface tension as a function of the frequency of bubble formation.

4. Apparatus according to claim 1 in which the automatic gas delivery means includes a supply of gas under pressure and in flow-series therewith a first flow-restricting capillary, an accumulator zone for storing gas from the first capillary, a second flow-restricting capillary, and a relatively unrestricted delivery tube connecting the second capillary to the bubble orifice tube.

5. Apparatus according to claim 4 in which the accumulator zone and the delivery tube are provided with atmospheric vents automatically closable to start bubble formation.

6. Apparatus for measuring dynamic surface tension at a gas-liquid interface by the maximum bubble-pressure method comprising
   a bubble orifice tube having non-wetted surfaces adapted to be immersed in the liquid at a predetermined depth;
   automatic gas delivery means including a supply of gas under pressure and in flow-series therewith a first flow-restricting capillary, an accumulator zone for storing gas from the first capillary, a second capillary of lower flow resistance than the first, a relatively unrestricted delivery tube connecting the second capillary to the bubble tube, and atmospheric vents for the accumulator zone and the delivery tube automatically closable to start bubble formation, such means delivering gas to the orifice tube at a rate rising steadily over an interval of time to increase the frequency of bubble formation at least several fold; and
   a bubble pressure measuring system including a pressure-measuring transducer in free communication with the bubble tube and providing electrical output instantaneously indicative of the pressure in each bubble, a peak-detecting circuit responsive to the transducer output providing a signal indicative of the maximum bubble pressure, a converter circuit responsive to the transducer output providing a signal indicative of the frequency of bubble formation, and a recorder responsive to the said two signals adapted to display a spectrum of the maximum bubble pressures in units directly indicative of surface tension as a function of the frequency of bubble formation.

7. In a method of measuring the dynamic surface tension at a liquid-gas interface by the maximum bubble-pressure method, wherein a flow of gas is passed through a bubble orifice immersed at a predetermined depth in the liquid, the improvement which comprises
   supplying the gas at a rate continually increasing over an interval of time to raise the frequency of bubble formation at least several fold, and
   measuring the maximum bubble pressures throughout the interval, each such maximum pressure being a function of the surface tension.

8. A method according to claim 7 in which a spectrum of maximum bubble pressure is recorded as a function of the frequency of bubbling.

9. A method according to claim 7 in which the time interval of gas rate rise is from about one to about three minutes and the frequency of bubbling is increased from less than one to at least ten hertz.

10. A method according to claim 9 in which a spectrum of maximum bubble pressure is recorded as a function of the frequency of bubbling over at least about a thousand bubbles.

11. A method according to claim 7 in which the gas is supplied by flowing it from a high pressure source through a first restriction, accumulating this restricted flow in a storage zone at a continuously rising pressure, and flowing a part of the accumulated gas through a second restriction to the bubble tube.

* * * * *